United States Patent
Milazzo et al.

(10) Patent No.: US 8,992,571 B2
(45) Date of Patent: Mar. 31, 2015

(54) SUTURE CLIP

(75) Inventors: David J. Milazzo, Santa Clara, CA (US); Aaron M. Fortson, Fremont, CA (US); Douglas H. Mehl, Redwood City, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 619 days.

(21) Appl. No.: 13/286,978

(22) Filed: Nov. 1, 2011

(65) Prior Publication Data

US 2013/0110164 A1    May 2, 2013

(51) Int. Cl.
*A61B 17/04* (2006.01)
*A61B 17/00* (2006.01)
*A61B 17/06* (2006.01)

(52) U.S. Cl.
CPC ... *A61B 17/0487* (2013.01); *A61B 2017/00004* (2013.01); *A61B 2017/00862* (2013.01); *A61B 2017/00867* (2013.01); *A61B 2017/00871* (2013.01); *A61B 2017/0462* (2013.01); *A61B 2017/0461* (2013.01); *A61B 2017/06176* (2013.01)
USPC .......................................................... 606/232

(58) Field of Classification Search
USPC ............ 606/151, 157, 158, 232, 148; 40/666; 24/129 R, 130, 30.5 S, 561, 562
See application file for complete search history.

(56) References Cited

U.S. PATENT DOCUMENTS

| | | | | |
|---|---|---|---|---|
| 2,847,774 A | * | 8/1958 | Brooks | 40/666 |
| 3,797,076 A | * | 3/1974 | Watkin | 24/562 |
| 3,931,821 A | * | 1/1976 | Kletschka et al. | 24/129 R |
| 4,598,708 A | * | 7/1986 | Beranek | 606/157 |
| 4,760,624 A | * | 8/1988 | Fish | 24/30.5 S |
| 4,823,794 A | * | 4/1989 | Pierce | 606/232 |
| 5,692,806 A | * | 12/1997 | Jones | 24/561 |
| 2010/0274283 A1 | * | 10/2010 | Kirsch et al. | 606/232 |

* cited by examiner

*Primary Examiner* — Julian W Woo
(74) *Attorney, Agent, or Firm* — Workman Nydegger; Randy S. Shen (57) ABSTRACT

A suture clip having a top surface and an opposing bottom surface with a perimeter sidewall extending therebetween. An aperture extends completely through the clip between the top and bottom surfaces to form a slot. The slot extends into the clip from a mouth at a periphery on a first end of the clip to divide the clip into first and second lateral portions that are separated at the first end but connected at a second end of the clip. The slot is bounded by opposing inner sidewalls of the first and second lateral portions extending between the top and bottom surfaces of the clip. The clip has a sufficient resilient force to allow a suture to be slid into the slot and has a sufficient clamping force to retain the suture in place within the slot once a desired positioned of the suture has been attained.

21 Claims, 5 Drawing Sheets

SUTURE CLIP

BACKGROUND OF THE INVENTION

1. The Field of the Invention

The present disclosure relates generally to systems for securing a pair of suture lengths together or for using a single strand of suture to secure tissues together in a patient without the need for tying a knot.

2. The Relevant Technology

During intravascular and other related medical procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance.

Often these procedures are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. The catheter typically is passed through the lumen of the introducer sheath and advanced over the guide wire into position for the medical procedure.

After the procedure is completed and the catheter and introducer sheath are removed from the patient, however, the access hole must be closed to prevent hemorrhage. This is typically achieved by applying pressure over the blood vessel manually and then by applying a pressure bandage or a compressive weight. With conventional methods, the rate of post-puncture hemorrhage is high, which can cause considerable complications. This impediment is exacerbated by the concomitant use of anticoagulant medications such as heparin or warfarin and by anti-platelet drugs, which are commonly used following a procedure in order to prevent clot formation and thrombus and/or to treat vascular disease.

In another common approach, one or more sutures are used to close the access hole. Typically, the surgeon manually ties together a suture pair to close the opening; however, automatic suture tying systems have also been developed.

Although using sutures have been found to be an effective way of closing an opening in tissue, there are a number of disadvantages of knotting sutures together to close the opening. For example, manual knot tying requires considerable dexterity. Also, manual knot tying can take considerable time. Knot tying is further complicated by the fact that surgical sutures have low friction surfaces. Therefore, it is typically necessary for a surgeon to include many "throws" when tying the knot. This multiple-throw problem occurs even if an automatic knot tying device is used. Unfortunately, as the number of loops or "throws" incorporated into the knot increases, the knot becomes increasingly large and bulky.

Moreover, the surgeon typically needs to handle strands of adequate suture length prior to commencing manual knot tying. Thus, manual knot tying requires considerable space both in which to view, and to perform, the actual suture knot tying. Therefore, knot tying is particularly difficult in areas of limited available space or access, such as, for example, at the back of the patient's heart during a coronary artery bypass graft (CABG) operation, or at the artery in the tissue tract after a femoral artery catheterization procedure.

Furthermore, manually tied knots often lock prior to reaching the intended amount of tension to be applied to the tissue, thereby potentially leading to an incomplete closure. This can be particularly important in sealing arterial punctures, which are relatively high pressure systems. For example, under normal blood pressure, the arterial system has a pressure of about 104/80 mmHg or more. Failure to completely close arterial holes can result in hematoma, exsanguination, and other catastrophic consequences, including limb amputation and death.

BRIEF SUMMARY

The present disclosure provides methods and apparatuses that are suitable for closure of vascular punctures or other openings in bodily tissues. In particular, the present disclosure includes suture clips and corresponding methods of use to tighten sutures about an opening to close the opening. In some embodiments, the suture clips are bioabsorbable.

In one aspect of the invention, there is provided a suture clip having a top surface and an opposing bottom surface with a perimeter sidewall extending therebetween. An aperture extends completely through the suture clip between the top and bottom surfaces so as to form a slot. The slot extends into the suture clip from a mouth at a periphery on a first end of the suture clip so as to divide the suture clip into first and second lateral portions that are separated at the first end but connected at an opposing second end of the suture clip. The slot is bounded by opposing inner sidewalls of the first and second lateral portions extending between the top and bottom surfaces of the suture clip. The suture clip has a sufficient resilient force to allow a suture to be slid into the slot and has a sufficient clamping force to retain the suture in place within the slot once a desired positioned of the suture has been attained.

In another aspect of the invention, there is provided a suture clip extending from a first end to a spaced apart second end. The suture clip includes first and second lateral portions each extending from the first end of the suture clip to the second end of the suture clip. The first and second lateral portions each have a top surface and an opposing bottom surface with a perimeter sidewall extending therebetween. The second lateral portion is connected to the first lateral portion at the second end of the suture clip. The suture clip also includes a slot formed between the first and second lateral portions so as to separate the first and second lateral portions at the first end of the suture clip. The slot has a mouth at a periphery at the first end of the suture clip and extends from the mouth towards the second end of the suture clip. The slot is bounded on either lateral side by opposing inner sidewalls of the first and second lateral portions. The suture clip has a sufficient resilient force to allow a suture to be slid into the slot and has a sufficient clamping force to retain the suture in place within the slot once a desired positioned of the suture has been attained In another aspect of the invention there is provided a method of closing an opening in a body tissue. The method includes the steps of piercing a suture through the tissue on opposing sides of the opening so that opposing ends of the suture extend away from the tissue; receiving the opposing ends of the suture within a slot of a suture clip; and moving the suture clip along the suture toward the opening until the suture clip abuts or is adjacent to the tissue surrounding the opening, thereby securing the suture clip to the tissue and closing the hole within the tissue. The step of receiving the opposing ends of the suture within a slot of a suture clip can include flexing opposing resilient lateral portions of the suture clip away from each other to widen the slot; positioning both ends of the suture within the widened slot; and allowing the resilient lateral portions of the suture clip to move back to the initial positions relative to each other after the suture has been positioned within the slot.

These and other advantages and features of the present disclosure will become more fully apparent from the following description and appended claims, or may be learned by the practice of the disclosure as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

DETAILED DESCRIPTION

As used in the specification and appended claims, directional terms, such as "top," "bottom," "up," "down," "upper," "lower," "proximal," "distal," and the like are used herein solely to indicate relative directions in viewing the drawings and are not intended to limit the scope of the claims in any way.

The present disclosure provides methods and apparatuses that are suitable for closure of vascular punctures or other openings in bodily tissues. The devices and methods described herein are configured for wound closure on the external surface of the wound, which allows wound healing with little endothelial disruption thereby reducing the chances of intravascular thrombosis or embolism or intimal hyperplasia. In some embodiments, the closure elements are bioabsorbable.

Generally, the apparatuses and methods described herein can be used with any type of body tissue that has sufficient strength to be held together by the tissue closure devices described hereinafter. By way of example only, embodiments of the present invention can be used to close openings in tissues that have a wall or membrane function, e.g, pulmonary, intestinal, vascular, urethral, gastric, renal or other wall structures, or in membranes, e.g., amniotic or pericardial membranes. Openings in other types of tissues can also be closed using embodiments of the present invention. Although many types of body tissue can be closed by the methods and apparatuses disclosed herein, the description included herein refers to "vessels" for convenience.

Furthermore, the apparatuses and methods described herein can be used with large and small hole punctures or other openings in the body tissue. By way of example, the suture clips of the present invention can be sized to close holes from 5 French to 30 French or larger. It may also be possible to close holes of other sizes.

The present disclosure relates to devices, systems, and methods for closing an opening in a body tissue. More specifically, the present disclosure relates to clips that can be used in conjunction with sutures to close the opening. The suture clips may be compatible with a variety of sizes of body tissue openings.

Figure 1A:
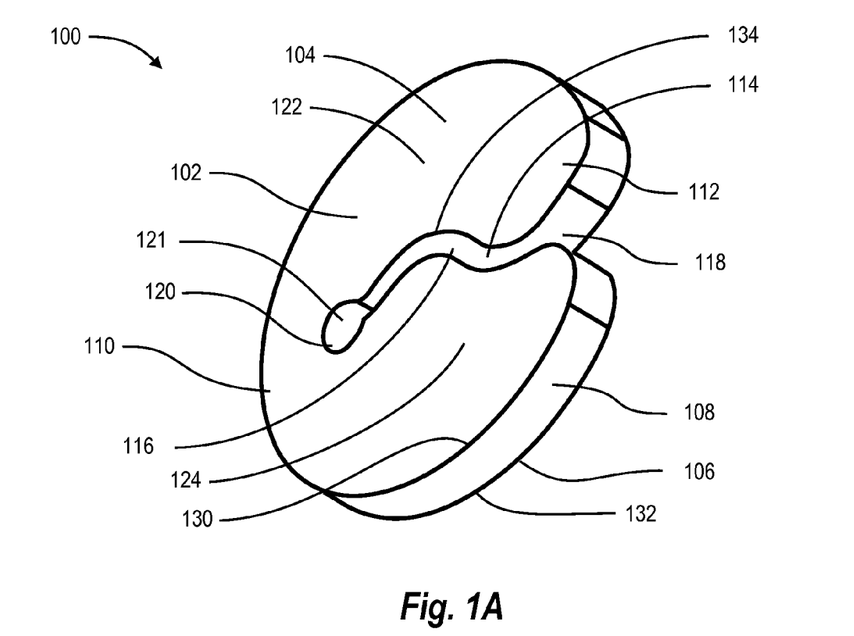
FIGS. 1A and 1B are top and bottom perspective views, respectively, of a suture clip according to one embodiment.
Figure 1B:
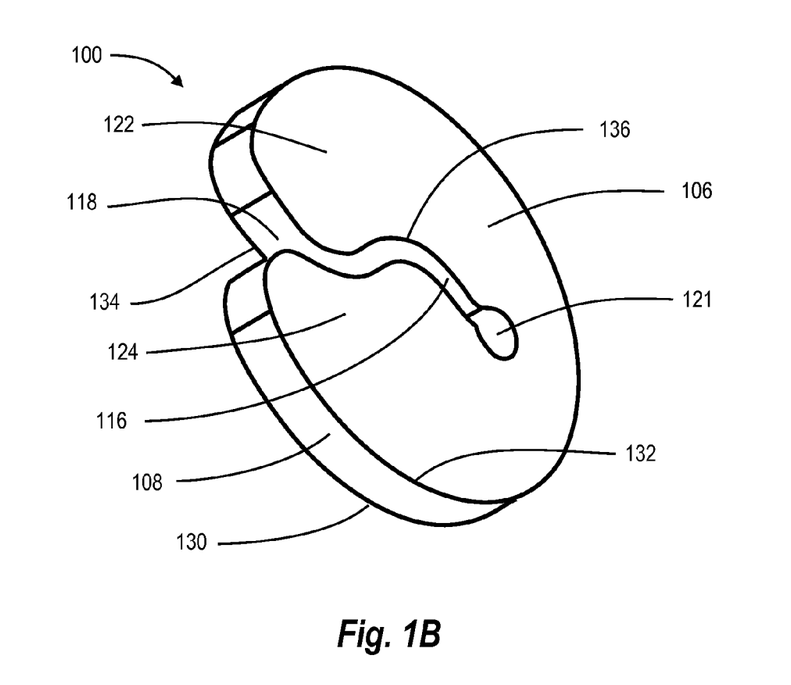
Figure 1C:
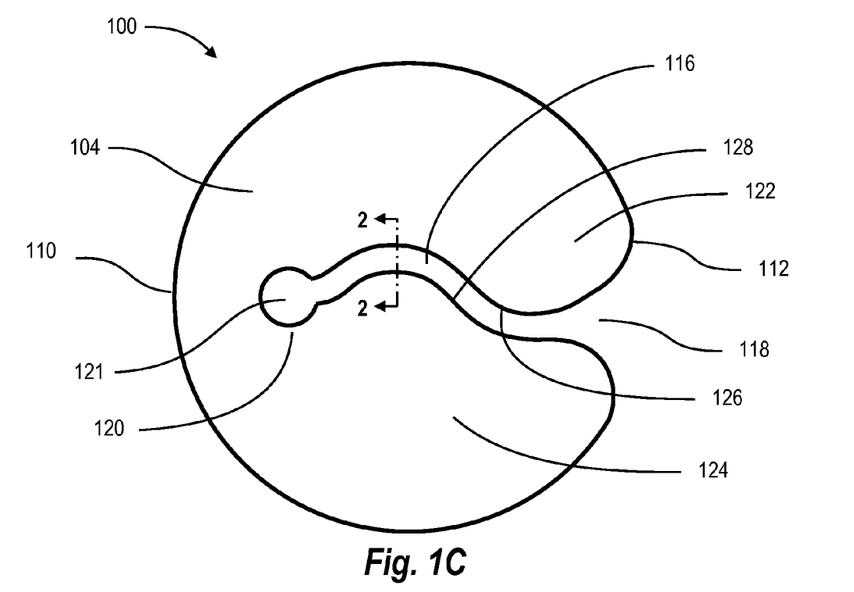
FIG. 1C is a top plan view of the suture clip of FIGS. 1A and 1B.

Turning now to the drawings, FIGS. 1A-1C illustrate a suture clip 100 in accordance with one embodiment. Suture clip 100 is configured to "tie off" a suture without requiring a knot to be formed in the suture. For example, suture clip 100 can be used with a suture to close an opening in a body tissue, as discussed below. Suture clip 100 has a substantially disk-shaped body 102, having a top surface 104 and an opposing bottom surface 106 extending between a first end 112 and a spaced apart second end 110. As shown in the depicted embodiment, top and bottom surfaces 104 and 106 can be substantially flat and parallel with each other, although that is not required. A perimeter sidewall 108 extends between the top and bottom surfaces 104 and 106. Perimeter sidewall 108 can be substantially straight and orthogonal between top and bottom surfaces 104 and 106 so as to form sharp edges 130 and 132 therebetween, or can be substantially curved. Other possible shapes for perimeter sidewall 108 can also be used.

An aperture 114 can extend completely through body 102 between top and bottom surfaces 104 and 106 so as to form a slot 116. Slot 116 extends into disk-shaped body 102 from a mouth 118 at a periphery at first end 112 of body 102 to an end 120. Slot 116 can be substantially linear or non-linear as it extends into body 102 from mouth 118. For example, in the depicted embodiment, slot 116 is generally "s" shaped. Other shapes are also possible. In addition, slot 116 can have a substantially same width as it extends into body 102 from mouth 118, or the width can vary along slot 116. Slot 116 can include an enlarged mouth 118 and/or an opening anywhere along slot 116 to aid in receiving and securing a suture within slot 116, as discussed in more detail below. For example, in the depicted embodiment, an enlarged opening 121 is formed at the end 120 of slot 116.

Enlarged opening 121 can aid in allowing more flexibility in suture clip body 102 at second end 110. Opening 121 can also provide a degree of protection against suture clip 100 forming cracks or breaking at second end 110 of body 102. In one embodiment, enlarged opening 121 is sized so as to have a smaller diameter than the suture to be used with suture clip 100. In those embodiments, the suture can be positioned and retained within opening 121 during use. In some embodiments, opening 121 has a larger diameter than the suture. In those embodiments, a protrusion or other feature can be formed within slot 116 that prevents the suture from entering opening 121.

Slot 116 can divide body 102 into a pair of lateral portions 122 and 124 that are connected at second end 110 of body 102. First and second lateral portions 122 and 124 respectively include inner sidewalls 126 and 128 that together bound and define slot 114. Inner sidewalls 126 and 128 each extend between a top edge 134 at top surface 104 and a bottom edge 136 at bottom surface 106.

Figure 2A:
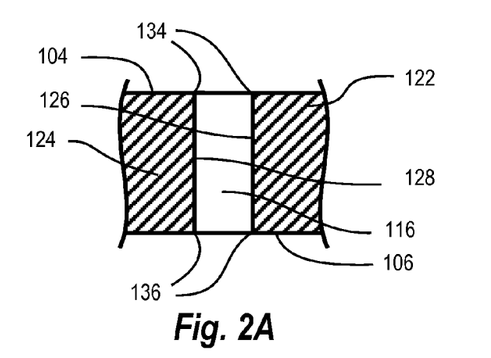
FIG. 2A-2E are cross sectional side views of the slot shown in FIG. 1C, taken along section line 2-2, showing shapes of the sidewalls that bound the slot for various embodiments.
Figure 2B:
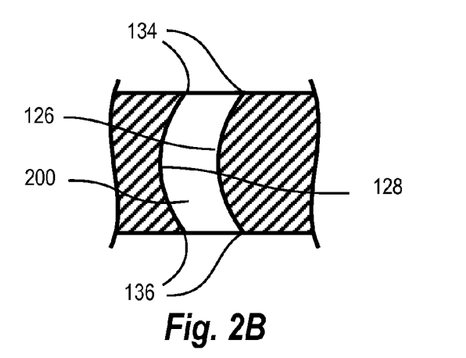
Figure 2C:
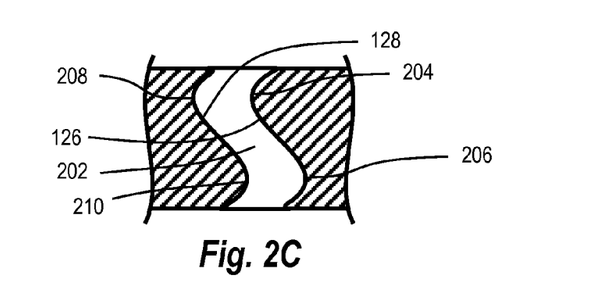
Figure 2D:
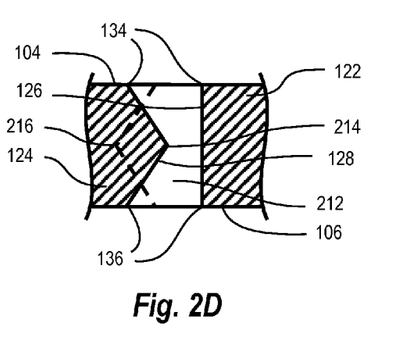
Figure 2E:
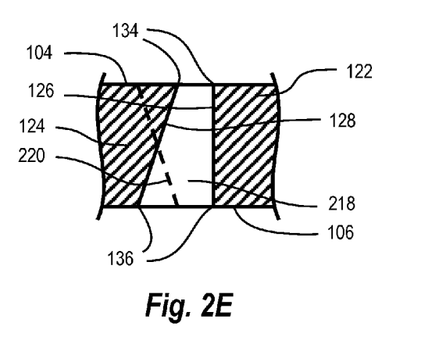

Similar to perimeter sidewall 108, inner sidewalls 126 and 128 can be substantially straight and orthogonal between top and bottom surfaces 104 and 106, or can be substantially curved or angled. For example, FIGS. 2A-2E show various sidewall shapes that can be used to form slot 116. In FIG. 2A, sidewalls 126 and 128 are both substantially orthogonal to top and bottom surfaces 104 and 106 so as to form substantially right angled edges 134 and 136 therebetween. Alternatively, FIGS. 2B and 2C show slots in which sidewalls 126 and 128 have matching curves and FIGS. 2D and 2E show slots in which sidewalls 126 and 128 are dissimilarly shaped to aid in securing a suture within slot 116.

FIG. 2B, for example, shows a slot 200 in which sidewall 126 has a convex curvature so that sidewall 126 extends laterally into slot 200 from top and bottom edges 134 and 136. Conversely, sidewall 128 has a matching concave curvature in which sidewall 128 retracts further into body 102 than at top and bottom edges 134 and 136. As a result, slot 116 can be generally "c"-shaped, as shown in FIG. 2B. Of course, the shapes of the sidewalls can be reversed so that sidewall 128 has the convex curvature and sidewall 126 has the matching concave curvature, if desired. In an alternative embodiment, both sidewalls 126 and 128 can have opposite curvatures. For example, both sidewalls 126 and 128 can have convex or concave curvatures so the sidewalls are either closer together or farther apart at the center sections thereof then at the top and bottom edges 134 and 136.

FIG. 2C shows an example of a slot 202 having matching compound curves. The additional curves can form a more torturous path for the suture, thereby aiding in securing the suture within slot 116. In FIG. 2C, sidewall 126 has a convex portion 204 and a concave portion 206. Sidewall 128 has a matching concave portion 208 and convex portion 210. Concave and convex portions 208 and 210 of sidewall 128 are formed to respectively laterally align with convex and concave portions 204 and 206 of sidewall 126. As a result, slot 202 can be generally "s"-shaped, as shown in FIG. 2C. Of course, the shapes of the sidewalls can be reversed so as to form a generally backwards "s".

FIG. 2D shows an example of a slot 212 in which sidewall 126 is substantially orthogonal to top and bottom surfaces 104 and 106 while sidewall 128 comes to a peak 214 between top and bottom surfaces 104 and 106. As a result, sidewall 128 is closest to sidewall 126 at peak 214 and furthest from sidewall 126 at top and bottom edges 134 and 136. In an alternative embodiment, sidewall 128 has a valley 216 (shown in dashed line) instead of a peak. In that embodiment, sidewall 128 is closest to sidewall 126 at at top and bottom edges 134 and 136 and furthest from sidewall 126 at valley 216. Of course, the shapes of the sidewalls can be reversed so that sidewall 126 has the peak or valley, if desired.

FIG. 2E shows an example of a slot 218 in which sidewall 126 is substantially orthogonal to top and bottom surfaces 104 and 106 while sidewall 128 angles away from sidewall 126 between top and bottom surfaces 104 and 106. As a result, sidewall 128 is closest to sidewall 126 at top edges 134 and furthest from sidewall 126 at bottom edges 136. In an alternative embodiment, sidewall 128 is angled toward sidewall 126 between top and bottom surfaces 104 and 106, as shown by dashed line 220. In that embodiment, sidewall 128 is closest to sidewall 126 at bottom edges 136 and furthest from sidewall 126 at top edges 134. Of course, the shapes of the sidewalls can be reversed so that sidewall 126 is angled, if desired. In alternative embodiments, both of the sidewalls 126 and 128 can be angled.

It is appreciated that the above slot shapes are exemplary only and that other slot shapes can alternatively be used. For example, any of the above slot shapes can be mixed and matched on either surface in any combination, Other slot shapes can also be used.

Figure 3:
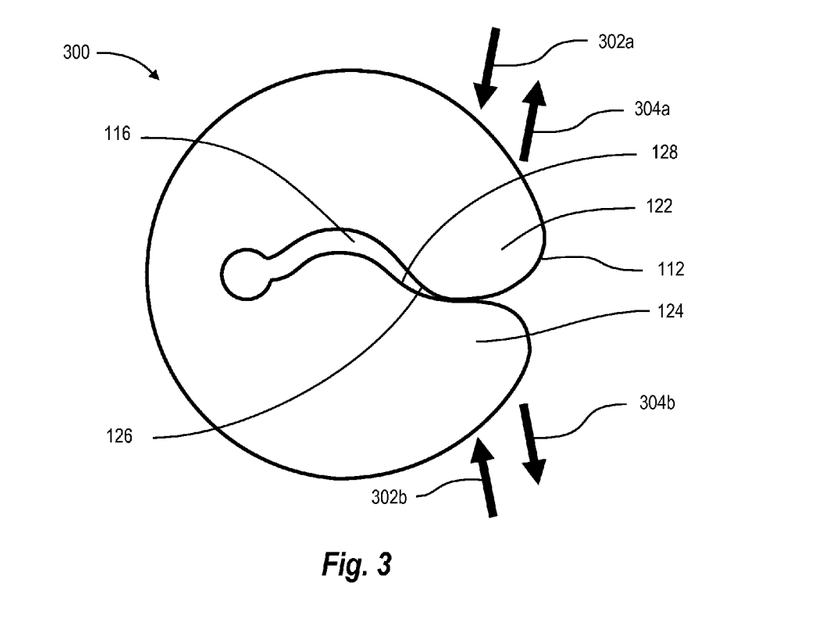
FIG. 3 is a top view of the clip shown in FIGS. 1A-1C, illustrating the clip in a closed configuration.

In the above discussed embodiments, slot 116 is configured to remain open, as shown in FIG. 1C, before and after receiving any sutures. That is, inner sidewalls 126 and 128 are configured to remain separated from each other along the length of slot 116. In an alternative embodiment, the slot is able to move between the open position and a closed position in which at least a portion of the opposing inner sidewalls contact each other. For example, FIG. 3 shows an embodiment of a suture clip 300 in a closed position. In FIG. 3, inner sidewalls 126 and 128 have been moved inward to contact each other and close slot 116 near first end 112. The open position of suture clip 300 can be similar to suture clip 100. That is, suture clip 300 can be similar to suture clip 100 shown in FIGS. 1A-1C in the open configuration. In contrast to suture clip 100, however, suture clip 300 can also move to the closed configuration shown in FIG. 3.

In one embodiment suture clip 300 can remain in the open position until moved by opposing forces (represented as arrows 302a and 302b) to push first and second lateral portions 122 and 124 together to close at least part of the slot 116 between them. In one embodiment, when the opposing joining forces 302 are removed, suture clip 300 can remain in the closed position depicted. In an alternative embodiment suture clip 300 can be resilient such that suture clip 300 can automatically move back to the open position when the opposing joining forces 302 are removed.

In an alternative embodiment, suture clip 300 can remain in the closed position depicted until moved by opposing forces (represented by arrows 304a and 304b) to separate first and second lateral portions 122 and 124 to open at least a portion of the slot 116 between them. In one embodiment, when the opposing separating forces 304 are removed, suture clip 300 can remain in the open position. In an alternative embodiment suture clip 300 can be resilient such that suture clip 300 can automatically move back to the closed position when the opposing separating forces are removed.

Having a closed position may help clip 300 retain a suture that passes through slot 116. The force that automatically closes slot 116 can also cause suture to remain within slot 116. Whether suture clip 300 remains in the open or closed position or automatically returns to the opposite position will likely depend on the materials that are included in suture clip 300. For example, suture clip 300 may include any of a number of shape memory and/or superelastic materials and may be set to elastically return to the open or closed configuration from any other configuration. In one embodiment, the closure element includes nitinol. Exemplary materials for the suture clamps envisioned herein are given below.

Figure 4:
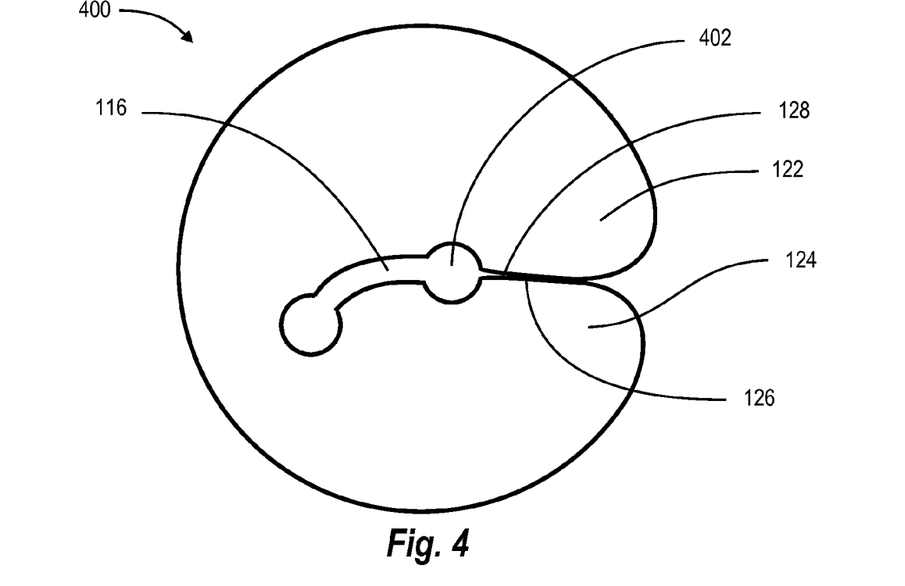
FIG. 4 is a top view of a suture clip according to another embodiment.

FIG. 4 shows another embodiment of a suture clip 400 in a closed configuration. Suture clip 400 includes an enlarged opening 402 midway along slot 116 that can allow more flexibility in suture clip 400 when pushing first and second lateral portions 122 and 124 together. As a result, a greater portion of opposing inner sidewalls 126 and 128 can contact each other in the closed position. Similar to suture clip 300, in some embodiments, suture clip 400 can remain in the open or closed configuration and in other embodiments, suture clip 400 can automatically return to the opposite configuration when the opposing forces are removed. Similar to opening 121, opening 402 can be sized to retain the suture therein, or can be sized larger than the suture and one or more features can be formed on slot 116 to prevent the suture from entering opening 402.

Figure 5:
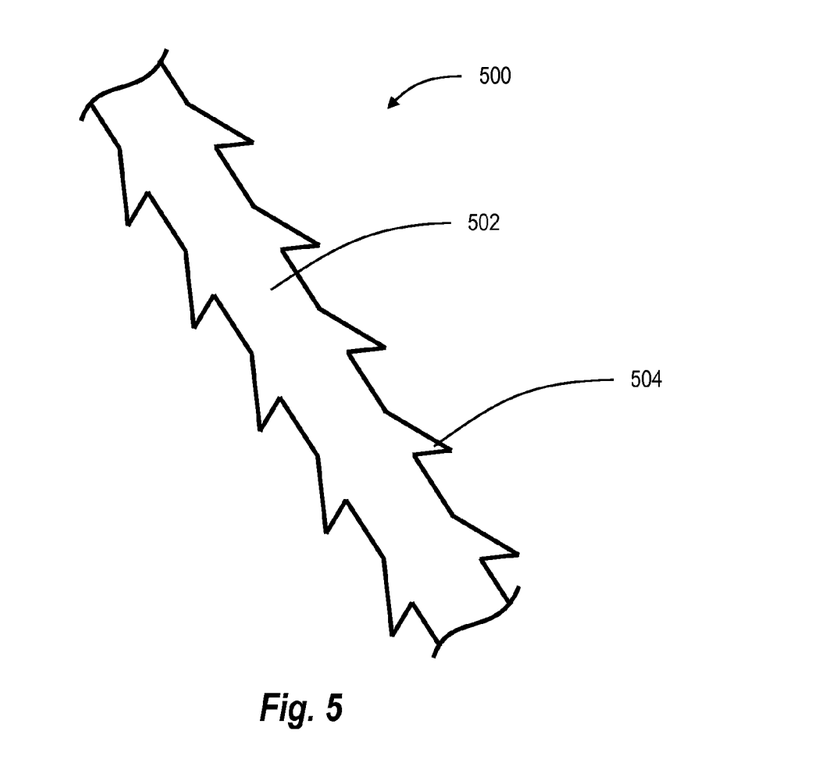
FIG. 5 is a perspective view of a suture that can be used with the suture clips disclosed herein.

In one embodiment, retention members can be included on the suture that is passed through the slot of the suture clip to help the suture clip retain the suture within the slot. For example, FIG. 5 shows a suture 500 having a longitudinal body 502 with retention members in the form of a plurality of barbs 504 formed along the length thereof. Barbs 504 can be generally shaped so as to extend radially away from longitudinal body 502. Barbs 504 can be formed so as to extend around the entire circumference of suture 500 or any portion thereof. In one embodiment, a barb 504 can be positioned on either lateral side of suture 500 so as to be diametrically opposed to each other. Other configurations can also be used.

As suture 500 is received and pulled through any of the suture clip slots discussed herein, barbs 504 necessarily also pass through the slot. Once pulled through the slot, barbs 504 can then catch on top edges 134 of inner sidewalls 126 and/or 128 (FIG. 2A) to help prevent suture 500 from slipping back out through the slot. Other types of retention members can alternatively be used.

The suture clips disclosed herein can be made of a single material or of multiple materials. This can include a metal primary material and polymer/drug topcoat or a different metal top layer. The multiple layers can be made of resiliently flexible materials or rigid and inflexible materials, and selected combinations thereof. The use of resiliently flexible materials can provide force-absorbing characteristics, which can also be beneficial for absorbing stresses and strains, which may inhibit crack formation at high stress zones. Also, the multiple layers can be useful for applying radiopaque materials.

Embodiments of the suture clip can be comprised of a biocompatible material. Examples of such materials include stainless steel, titanium, and nickel titanium alloys. In addition, embodiments of the suture clip can be comprised of a bioabsorbable material. Examples of such materials include PGA and magnesium alloys. Other materials are also possible. By being comprised of a bioabsorbable material, the suture clip may dissolve and become absorbed into the body after the opening in the tissue has been closed. Because the suture clip may be absorbed into the body, the surgeon in future procedures will not be prevented from reaccessing a similar area of the tissue as is the case with many conventional clips.

Embodiments of the suture clip can be comprised of a material made from any of a variety of known suitable biocompatible materials, such as a biocompatible shape memory material (SMM). SMMs have a shape memory effect in which they can be made to remember a particular shape. Once a shape has been remembered, the SMM may be bent out of shape or deformed and then returned to its original shape by unloading from strain or heating. Typically, the SMMs can be shape memory alloys (SMA) comprised of metal alloys, or shape memory plastics (SMP) comprised of polymers. The materials can also be referred to as being superelastic.

Some examples of SMAs that can be used with the embodiments of the present application include, but are not limited to: copper-zinc-aluminum; copper-aluminum-nickel; nickel-titanium (NiTi) alloys known as nitinol; nickel-titanium-platinum; nickel-titanium palladium; and cobalt-chromium-nickel alloys or cobalt-chromium-nickel-molybdenum alloys known as elgiloy alloys.

It can be beneficial to include at least one layer of an SMA and at least one layer of an SMP to form a multilayered body; however, any appropriate combination of materials can be used to form a multilayered device. Examples of SMPs that can be used in embodiments of the present application include, but are not limited to, biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present disclosure.

In one embodiment, the suture clip can be made at least in part of a high strength, low modulus metal alloy comprising Niobium, Tantalum, and at least one element selected from the group consisting of Zirconium, Tungsten, and Molybdenum.

In further embodiments, the suture clip can be made from or be coated with a biocompatible polymer. Examples of such biocompatible polymeric materials can include hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

Reference is now made to FIGS. 6A-6D, which illustrate a method of closing a tissue opening using suture clip 100 according to one embodiment.

Figure 6A:
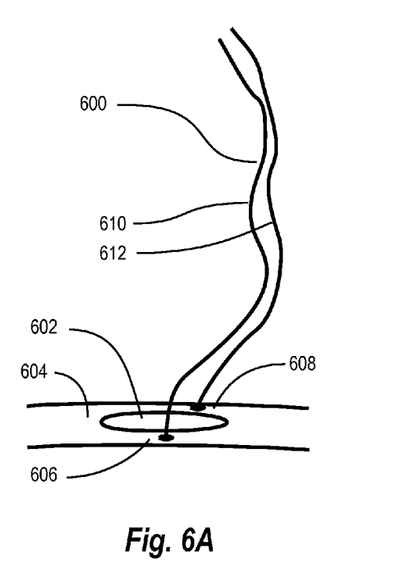
FIGS. 6A-6D illustrate one embodiment of a method of closing an opening in a body tissue using the suture clip of FIG. 1A.

As shown in FIG. 6A, a suture 600 is sewn or otherwise positioned across an opening 602 made in a tissue 604, such as a wall in a vein, artery, or other body vessel. The opening 602 may be a result, e.g., of a percutaneous medical procedure, another medical procedure requiring a tissue opening to be made, or an unintended gash or tear in a tissue. As is known in the art, a needle can be used to pierce tissue 604 on a lateral side 606 of the opening 602 and force suture 600 through tissue 604 between the outer and inner surfaces of the tissue. The needle can then span laterally across opening 602 on the inner side of tissue 604, then force suture 600 back through the inner and outer surfaces of the tissue on the opposite lateral side 608 of opening 602. In this manner, opposing ends 610 and 612 of the suture can extend away from the outer surface of the tissue, as shown in FIG. 6A. As discussed above, a suture having barbs or other types of retention members can be used, if desired.

Figure 6B:
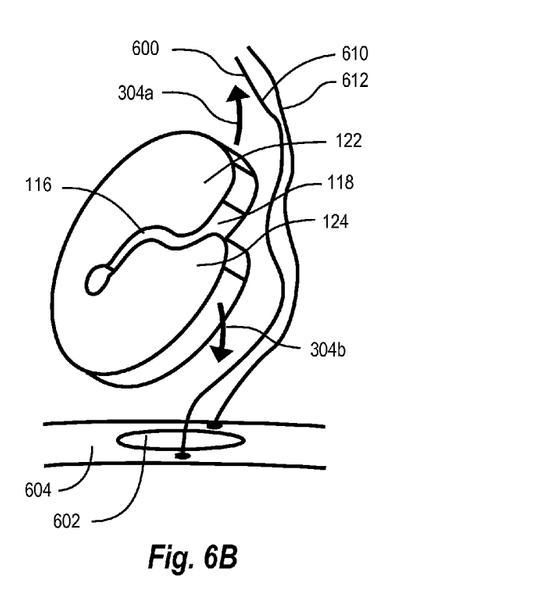
Figure 6C:
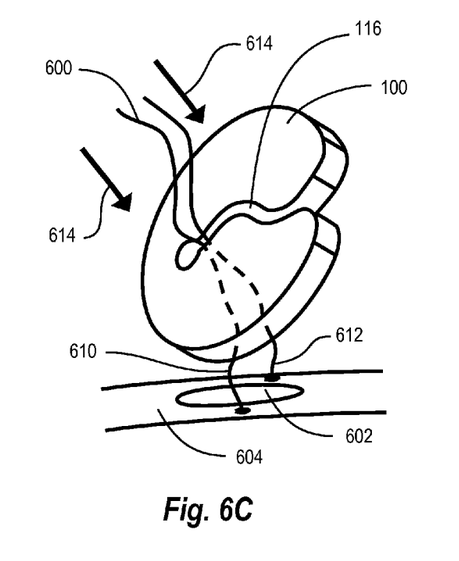

As shown in FIG. 6B, once suture 600 has been sewn through tissue 604, suture clip 100 can be used to "tie off" the suture. To do so, both ends 610 and 612 of suture 600 can be received within slot 116 of suture clip 100. This can be done by laterally inserting both ends 610 and 612 of suture 600 into slot 116 through mouth 118 thereof and moving both ends 610 and 612 further into slot 116. If needed, opposing lateral separating forces, denoted by arrows 304a and 304b, can be used to force first and second lateral portions 122 and 124 apart so that suture 600 can be more easily inserted into slot 116, as discussed above. This may be required if the slot of the suture clip is biased to a closed configuration (see, e.g., FIGS. 3 and 4) when no force is applied. In some embodiments, once suture 600 is positioned within slot 116, lateral separating forces 304a and 304b can be removed from first and second lateral portions 122 and 124, thereby causing first and second lateral portions 122 and 124 to return laterally to their closed positions to secure suture 600 therein.

In some embodiments suture clip 100 can receive suture 600 in slot 116 before suture clip 100 is inserted into the tissue tract of the body corresponding to the position of the opening 602. In other embodiments, suture 600 is not received within slot 116 until the suture clip has been inserted into the tissue tract. Regardless, once suture 600 has been received within slot 116, suture clip 100 can then be moved along suture 600 toward opening 602, as denoted by arrows 614 shown in FIG. 6C. As suture clip 100 is moved toward opening 602, the ends 610 and 612 of suture 600 are held in place, thereby causing suture clip 100 to move along suture 600. That is, as suture clip 100 moves towards opening 602, suture 600 is drawn through slot 116, such that the amount of suture 600 disposed between suture clip 100 and the outer surface of tissue 604 lessens as suture clip 100 nears opening 602.

Figure 6D:
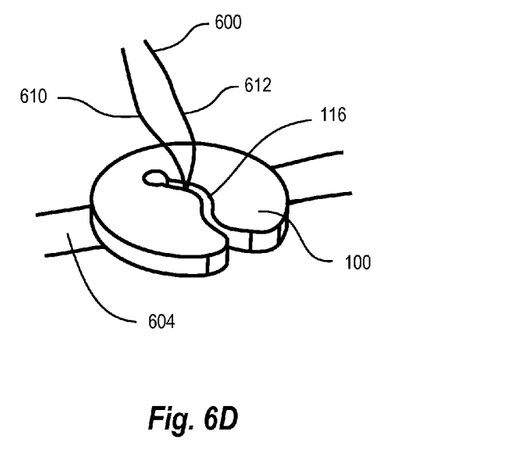

As shown in FIG. 6D, as suture clip 100 nears opening 602, both ends 610 and 612 of suture 600 gather together within slot 116 of suture clip 100 adjacent opening 602. This causes the suture to tighten about opening 602. As a result of the tightening, the opening 602 begins to close. Suture clip 100 can be further advanced toward opening 602 until suture clip 100 abuts or is adjacent to the outer surface of tissue 604 around opening 602. Once suture clip 100 is in this final position, both ends 610 and 612 of suture 600 can be moved further outward from suture clip 100 (i.e., away from tissue 604) to close opening 602 within tissue 604 and secure suture 600 to tissue 604. As noted above, in some embodiments, barbs can be included on suture 600 to aid in securing suture 600 within slot 116. In some embodiments, suture 600 can be tied off in addition to using suture clip 100.

It is appreciated that the above described method is exemplary only and that other methods can be used to close an opening within tissue using any of the suture clips envisioned in the present application. For example, in one embodiment one or more additional sutures can be used in addition to suture 600. In that case, the ends of all of additional sutures can also be received within slot 116 of suture clip 100.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A resilient suture clip having a top surface and an opposing bottom surface with a perimeter sidewall extending therebetween, an aperture extending completely through the suture clip between the top and bottom surfaces so as to form a slot, the slot extending into the suture clip from a mouth at a periphery at a first end of the suture clip so as to divide the suture clip into first and second lateral portions that are separated at the first end but connected at an opposite second end of the suture clip, the slot being bounded by opposing inner sidewalls of the first and second lateral portions extending between the top and bottom surfaces of the suture clip, the slot including a first curve and a second curve connected at a singular point of inflection, the first curve is concave down and the second curve is concave up, the first and second curves being continuous along the length of the slot such that the entire slot is curved from the first end to the second end, the suture clip having a sufficient resilient force to allow a suture to be slid into the slot and having a sufficient clamping force to retain the suture in place within the slot once a desired positioned of the suture has been attained.

2. The suture clip recited in claim 1, wherein the suture clip is comprised of one or more shape memory materials.

3. The suture clip recited in claim 1, wherein the first lateral portion is integrally formed with the second lateral portion at the second end of the suture clip.

4. The suture clip recited in claim 1, wherein the first and second curves of the slot define a substantially "s"-shaped curve between the first and second ends.

5. The suture clip recited in claim 1, wherein the slot includes an enlarged opening formed therein.

6. The suture clip recited in claim 1, wherein the slot has a width that is substantially the same along the length of the slot.

7. The suture clip recited in claim 1, wherein the inner sidewalls that bound the slot have substantially c-shaped cross sections between the top and bottom surfaces of the suture clip.

8. The suture clip recited in claim 1, wherein the inner sidewalls that bound the slot have compound curves between the top and bottom surfaces of the suture clip.

9. The suture clip recited in claim 1, wherein the suture clip is movable between:
   an open position, in which the opposing inner sidewalls are separated from each other; and
   a closed position, in which at least a portion of the opposing inner sidewalls contact each other to close the slot thereat.

10. The suture clip recited in claim 9, wherein the suture clip is configured to move to or remain in the closed position unless an external separating force is applied to the lateral portions of the suture clip.

11. The suture clip recited in claim 1, wherein the suture clip is resiliently flexible.

12. The suture clip recited in claim 1, wherein the suture clip is bioabsorbable.

13. A suturing system, comprising:
   a suture clip as recited in claim 1; and
   a suture receivable within the slot of the suture clip.

14. The suturing system recited in claim 13, wherein the suture includes a plurality of retention members extending therefrom that catch on an edge of the inner sidewalls that bound the slot to secure the suture to the clip.

15. A suture clip extending from a first end to a spaced apart second end, the suture clip comprising:
   a first lateral portion extending from the periphery at the first end of the suture clip to the second end of the suture clip, the first lateral portion having a top surface and an opposing bottom surface with a perimeter sidewall extending therebetween; and
   a second lateral portion extending from the first end of the suture clip to the second end of the suture clip, the second lateral portion also having a top surface and an opposing bottom surface with a perimeter sidewall extending therebetween, the second lateral portion being connected to the first lateral portion at the second end of the suture clip; and
   a slot formed between the first and second lateral portions so as to separate the first and second lateral portions at the first end of the suture clip, the slot having a mouth at the first end of the suture clip and extending from the mouth towards the second end of the suture clip, the slot being bounded on either lateral side by opposing inner sidewalls of the first and second lateral portions, the slot including a first curve and a second curve connected at a point of inflection, the first curve is concave down and the second curve is concave up, the first and second curves being continuous along the length of the slot such that the entire slot is curved from the first end to the second end, the suture clip having a sufficient resilient force to allow a suture to be slid into the slot in an open position and having a sufficient clamping force to retain the suture in place within the slot in a closed position once a desired positioned of the suture has been attained, the first lateral portion and the second lateral portion lying in the same plane when in both the open position and the closed position.

16. The suture clip recited in claim 15, wherein the suture clip is movable between:
   an open position, in which the opposing inner sidewalls are separated from each other; and
   a closed position, in which at least a portion of the opposing inner sidewalls contact each other to close the slot thereat.

17. The suture clip recited in claim 16, wherein the suture clip is configured to move to or remain in the closed position unless an external separating force is applied to the lateral portions of the suture clip.

18. The suture clip recited in claim 15, wherein the suture clip is resiliently flexible.

19. The suture clip recited in claim 1, further comprising a second aperture located in an intermediate section of the slot.

20. The suture clip recited in claim 1, wherein the opposing inner sidewalls include a first sidewall on the first lateral portion and a second sidewall on the second lateral portion, the first sidewall comes to a peak between the top and bottom surfaces of the suture clip.

21. The suture clip recited in claim 20, wherein the peak is equidistant between the top and bottom surfaces of the suture clip.

* * * * *